(12) United States Patent
Chanduszko

(10) Patent No.: US 8,361,110 B2
(45) Date of Patent: Jan. 29, 2013

(54) HEART-SHAPED PFO CLOSURE DEVICE

(75) Inventor: Andrzej J. Chanduszko, Chandler, AZ (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 634 days.

(21) Appl. No.: 11/111,675

(22) Filed: Apr. 21, 2005

(65) Prior Publication Data
US 2005/0267525 A1    Dec. 1, 2005

Related U.S. Application Data

(60) Provisional application No. 60/565,285, filed on Apr. 26, 2004.

(51) Int. Cl.
*A61B 17/08* (2006.01)
(52) U.S. Cl. .......................... 606/213; 606/151
(58) Field of Classification Search .................. 606/213, 606/151
See application file for complete search history.

(56) References Cited

U.S. PATENT DOCUMENTS

| | | |
|---|---|---|
| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi |
| 4,006,747 A | 2/1977 | Kronenthal et al. |
| 4,007,743 A | 2/1977 | Blake |
| 4,149,327 A | 4/1979 | Hammer et al. |
| 4,425,908 A | 1/1984 | Simon |
| 4,610,674 A | 9/1986 | Suzuki et al. |
| 4,626,245 A | 12/1986 | Weinstein |
| 4,696,300 A | 9/1987 | Anderson |
| 4,710,192 A | 12/1987 | Liotta et al. |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,956,178 A | 9/1990 | Badylak et al. |

(Continued)

FOREIGN PATENT DOCUMENTS

| | | |
|---|---|---|
| DE | 94 13 645 U1 | 10/1994 |
| DE | 9413645 U1 | 10/1994 |

(Continued)

OTHER PUBLICATIONS

Kimura, A., et al., "Effects of Neutron Irradiation on the Transformation Behavior in Ti-Ni Alloys," Abstract, Proceedings of the Int'Conf. on Mariensitic Transformations, 1992, pp. 935-940.

(Continued)

*Primary Examiner* — S. Thomas Hughes
*Assistant Examiner* — Julie A Szpira
(74) *Attorney, Agent, or Firm* — DLA Piper LLP (US)

(57) ABSTRACT

Patent foramen ovale (PFO) closure clip include two closure members, which may be heart shaped, joined by at least two spaced central connecting members. Each of the at least two spaced central connecting members is attached to each closure member at a location on the periphery of the closure member. The connecting member may be generally square shaped or include other shapes. The clips of the present invention may be formed of various materials, including metals, nonmetallic materials, bioresorbable polymers, spring steel, shape memory materials, bioresorbable shape memory polymers, or combinations thereof. The clips can take various forms depending, in part, upon the distribution of force required to close a given PFO. At least one of the closure members can include a tissue scaffold.

7 Claims, 8 Drawing Sheets

U.S. PATENT DOCUMENTS

| | | | |
|---|---|---|---|
| 5,021,059 A | 6/1991 | Kensey et al. |
| 5,037,433 A | 8/1991 | Wilk et al. |
| 5,041,129 A | 8/1991 | Hayhurst et al. |
| 5,078,736 A | 1/1992 | Behl |
| 5,106,913 A | 4/1992 | Yamaguchi et al. |
| 5,108,420 A | 4/1992 | Marks |
| 5,149,327 A | 9/1992 | Oshiyama |
| 5,167,363 A | 12/1992 | Adkinson et al. |
| 5,167,637 A | 12/1992 | Okada et al. |
| 5,171,259 A | 12/1992 | Inoue |
| 5,192,301 A | 3/1993 | Kamiya et al. |
| 5,222,974 A | 6/1993 | Kensey et al. |
| 5,226,879 A | 7/1993 | Ensminger et al. |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,334,217 A | 8/1994 | Das |
| 5,350,363 A | 9/1994 | Goode et al. |
| 5,354,308 A | 10/1994 | Simon et al. |
| 5,411,481 A | 5/1995 | Allen et al. |
| 5,413,584 A | 5/1995 | Schulze |
| 5,417,699 A | 5/1995 | Klein et al. |
| 5,425,744 A | 6/1995 | Fagan et al. |
| 5,433,727 A | 7/1995 | Sideris |
| 5,451,235 A | 9/1995 | Lock et al. |
| 5,478,353 A | 12/1995 | Yoon |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,562,632 A | 10/1996 | Davila et al. |
| 5,577,299 A | 11/1996 | Thompson et al. |
| 5,601,571 A | 2/1997 | Moss |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Scheidt |
| 5,709,707 A * | 1/1998 | Lock et al. ................ 606/213 |
| 5,717,259 A | 2/1998 | Schexnayder |
| 5,720,754 A | 2/1998 | Middleman et al. |
| 5,725,552 A | 3/1998 | Kotula et al. |
| 5,733,294 A * | 3/1998 | Forber et al. ............... 606/151 |
| 5,733,337 A | 3/1998 | Carr, Jr. et al. |
| 5,741,297 A | 4/1998 | Simon |
| 5,776,162 A | 7/1998 | Kleshinski |
| 5,776,183 A | 7/1998 | Kanesaka et al. |
| 5,797,960 A | 8/1998 | Stevens et al. |
| 5,800,516 A | 9/1998 | Fine et al. |
| 5,810,884 A | 9/1998 | Kim |
| 5,823,956 A | 10/1998 | Roth et al. |
| 5,829,447 A | 11/1998 | Stevens et al. |
| 5,853,420 A | 12/1998 | Chevillon et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stvrens et al. |
| 5,928,250 A | 7/1999 | Koike et al. |
| 5,944,738 A | 8/1999 | Amplatz et al. |
| 5,955,110 A | 9/1999 | Patel et al. |
| 5,976,174 A | 11/1999 | Ruiz |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,024,756 A | 2/2000 | Huebsch et al. |
| 6,030,007 A | 2/2000 | Bassily et al. |
| 6,056,760 A | 5/2000 | Koike et al. |
| 6,071,998 A | 6/2000 | Muller et al. |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,171,329 B1 | 1/2001 | Shaw et al. |
| 6,174,322 B1 | 1/2001 | Schneidt et al. |
| 6,174,330 B1 | 1/2001 | Stinson |
| 6,187,039 B1 | 2/2001 | Hiles et al. |
| 6,190,353 B1 | 2/2001 | Makower et al. |
| 6,206,895 B1 | 3/2001 | Levinson |
| 6,206,907 B1 | 3/2001 | Marino et al. |
| 6,214,029 B1 * | 4/2001 | Thill et al. ................ 606/213 |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,446 B1 | 11/2001 | Huebsch et al. |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,364,853 B1 | 4/2002 | French et al. |
| 6,371,904 B1 | 4/2002 | Sirimanne et al. |
| 6,375,625 B1 | 4/2002 | French et al. |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,419,669 B1 | 7/2002 | Frazier et al. |

| | | |
|---|---|---|
| 6,426,145 B1 | 7/2002 | Moroni |
| 6,436,088 B2 | 8/2002 | Frazier et al. |
| 6,440,152 B1 | 8/2002 | Gainor et al. |
| 6,460,749 B1 | 10/2002 | Levinson et al. |
| 6,482,224 B1 | 11/2002 | Michler et al. |
| 6,488,706 B1 | 12/2002 | Solymar |
| 6,494,888 B1 | 12/2002 | Laufer et al. |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,585,755 B2 | 7/2003 | Jackson et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,666,861 B1 | 12/2003 | Grabek |
| 6,669,722 B2 | 12/2003 | Chen et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,867,249 B2 | 3/2005 | Lee et al. |
| 6,921,410 B2 | 7/2005 | Porter |
| 7,780,700 B2 * | 8/2010 | Frazier et al. .................. 606/216 |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Borillo et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0120337 A1 | 6/2003 | Van Tassel et al. |
| 2003/0139819 A1 | 7/2003 | Beer et al. |
| 2003/0171774 A1 | 9/2003 | Freudenthal et al. |
| 2003/0191495 A1 * | 10/2003 | Ryan et al. ..................... 606/213 |
| 2003/0195530 A1 | 10/2003 | Thill |
| 2003/0204203 A1 | 10/2003 | Khairkhahan et al. |
| 2003/0225421 A1 * | 12/2003 | Peavey et al. .................. 606/151 |
| 2004/0044361 A1 | 3/2004 | Frazier et al. |
| 2004/0073242 A1 * | 4/2004 | Chanduszko .................. 606/157 |
| 2004/0176799 A1 | 9/2004 | Chanduszko et al. |
| 2004/0210301 A1 | 10/2004 | Obermiller |
| 2004/0234567 A1 | 11/2004 | Dawson |
| 2005/0025809 A1 | 2/2005 | Hasirci et al. |
| 2005/0043759 A1 | 2/2005 | Chanduszko |
| 2005/0113868 A1 | 5/2005 | Devellian et al. |
| 2005/0267523 A1 | 12/2005 | Devellian et al. |
| 2005/0273135 A1 | 12/2005 | Chanduszko et al. |
| 2005/0288786 A1 | 12/2005 | Chanduszko |
| 2006/0122647 A1 | 6/2006 | Callaghan et al. |
| 2006/0265004 A1 | 11/2006 | Callaghan et al. |
| 2007/0010851 A1 | 1/2007 | Chanduszko et al. |
| 2007/0167981 A1 | 7/2007 | Opolski |

FOREIGN PATENT DOCUMENTS

| | | |
|---|---|---|
| EP | 0 362 113 | 4/1990 |
| EP | 0362113 A1 | 4/1990 |
| EP | 0 474 887 | 3/1992 |
| EP | 0474887 A1 | 3/1992 |
| EP | 0 839 549 | 5/1998 |
| EP | 0 861 632 | 9/1998 |
| EP | 1 013 227 A2 | 6/2000 |
| EP | 1013227 A2 | 6/2000 |
| EP | 1 046 375 | 10/2000 |
| EP | 1046375 A1 | 10/2000 |
| EP | 1 222 897 | 7/2002 |
| EP | 1222897 A2 | 7/2002 |
| WO | WO-96/25179 | 8/1996 |
| WO | WO-96/25179 A1 | 8/1996 |
| WO | WO-96/31157 | 10/1996 |
| WO | WO-96/31157 A1 | 10/1996 |
| WO | WO-98/07375 A1 | 2/1998 |
| WO | WO-98/08462 | 3/1998 |
| WO | WO-98/16174 | 4/1998 |
| WO | WO-98/29026 A2 | 7/1998 |
| WO | WO-98/51812 | 11/1998 |
| WO | WO-99/05977 | 2/1999 |
| WO | WO-99/05977 A1 | 2/1999 |
| WO | WO-98/18864 | 4/1999 |
| WO | WO-99/18862 A1 | 4/1999 |
| WO | WO-99/18864 A1 | 4/1999 |
| WO | WO-99/18870 A1 | 4/1999 |
| WO | WO-99/18871 A1 | 4/1999 |
| WO | WO-99/30640 | 6/1999 |
| WO | WO-00/27292 | 5/2000 |
| WO | WO-00/27292 A1 | 5/2000 |
| WO | WO-00/44428 | 8/2000 |
| WO | WO-00/44428 A1 | 8/2000 |
| WO | WO-01/19256 | 3/2001 |
| WO | WO-01/21247 | 3/2001 |
| WO | WO-01/21247 A1 | 3/2001 |
| WO | WO-01/28432 | 4/2001 |
| WO | WO-01/30268 | 5/2001 |
| WO | WO-01/30268 A1 | 5/2001 |
| WO | WO-01/49185 | 7/2001 |
| WO | WO-01/49185 A1 | 7/2001 |
| WO | WO-01/78596 | 10/2001 |
| WO | WO-01/78596 A1 | 10/2001 |
| WO | WO-02/17809 | 3/2002 |
| WO | WO-02/17809 A1 | 3/2002 |
| WO | WO-02/24106 | 3/2002 |
| WO | WO-02/24106 A1 | 3/2002 |

| | | |
|---|---|---|
| WO | WO-03/024337 | 3/2003 |
| WO | WO-03/053493 A1 | 7/2003 |
| WO | WO-03/059152 | 7/2003 |
| WO | WO-03/077733 | 9/2003 |
| WO | WO-03/077733 A2 | 9/2003 |
| WO | WO-03/082076 | 10/2003 |
| WO | WO-03/103476 A | 12/2003 |
| WO | WO-03/103476 A2 | 12/2003 |
| WO | WO-2004/032993 | 4/2004 |
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

Meier, MD, Bernhard et al., "Contemporary Management of Patent Foramen Ovale," American Heart Association, Inc., Circulation, 2003, vol. 107, pp. 5-9.

Nat'l Aeronautics and Space Administration, "55-Nitinol—The Alloy with a Memory: Its Physical Metallurgy, Properties and Applications," NASA Report, pp. 24-25. Oct. 25, 2002.

Shabalovskaya, S., "Surface, Corrosion and Biocompatibility Aspects of Nitinol as an Implant Material," Bio-Medical Materials and Engineering, 2002, vol. 12, pp. 69-109.

SMST-2000, "Proceedings of the International Conference on Shape Memory and Superelastic Technologies," Apr. 30-May 4, 2000, Asilomar Conference Center.

Athanasion, T., "Coronary Artery Bypass with the Use of a Magnetic Distal Anastomotic Device: Surgical Technique and Preliminary Experience," The Heart Surgery Forum #2004-1024, 2004, 4 pgs.

Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.

European Examination Report, European Application No. 04781644.2, mailed Aug. 23, 2007 (3 Pages).

Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.

Filsoufi, F., et al., "Automated Distal Coronary Bypass with a Novel Magnetic Coupler (MVP system)," J. Thoracic and Cardiovascular Surgery, vol. 127(1), pp. 185-192.

International Search Report, International Application No. PCT/US02/40850 mailed Jun. 19, 2003 (4 pgs).

International Search Report, International Application No. PCT/US03/01050, mailed Jul. 8, 2003 (1 pg).

International Search Report, International Application No. PCT/US03/09051, mailed Sep. 29, 2003 (2 pgs).

International Search Report, International Application No. PCT/US03/17390, mailed Oct. 6, 2003 (4 pgs).

International Search Report, International Application No. PCT/US03/17715, mailed Mar. 24, 2004 (2 pgs).

International Search Report, International Application No. PCT/US03/32133, mailed Apr. 22, 2004 (1 pg).

International Search Report, International Application No. PCT/US03/34003 mailed Oct. 3, 2004 (4 pgs).

International Search Report, International Application No. PCT/US03/35479, mailed Apr. 14, 2004 (2 pgs).

International Search Report, International Application No. PCT/US03/35998 mailed Jun. 16, 2004 (5 pgs).

International Search Report, International Application No. PCT/US03/39253, mailed Apr. 19, 2004 (4 pgs).

International Search Report, International Application No. PCT/US04/022643, mailed Mar. 31, 2005 (2 pgs).

International Search Report, International Application No. PCT/US04/026998, mailed Apr. 22, 2005 (5 pgs).

International Search Report, International Application No. PCT/US04/029978, mailed Jan. 26, 2005 (3 pgs).

International Search Report, International Application No. PCT/US05/006703, mailed Jul. 25, 2005 (3 pgs).

International Search Report, International Application No. PCT/US05/013705 mailed Aug. 4, 2005 (4 pgs).

International Search Report, International Application No. PCT/US05/015382, mailed Oct. 6, 2005 (4 pgs).

International Search Report, International Application No. PCT/US07/065546, mailed Oct. 29, 2007. 4 pages.

International Search Report, International Application No. PCT/US2007/065526, mailed Aug. 8, 2007 (5 pgs).

International Search Report, International Application No. PCT/US2007/065541, mailed Aug. 7, 2007 (4 pgs).

International Search Report, International Application No. PCT/US97/14822, mailed Feb. 20, 1998 (2 pgs).

International Search Report, International Application No. PCT/US97/17927, mailed Feb. 10, 1998 (1 pg).

Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.

Kimura, A., et al., "Effects of Neutron Irradiation on the Transformation Behavior in Ti-Ni Alloys," Abstract, Proceedings of the Int'l Conf. on Mariensitic Transformations, 1992, pp. 935-940.

Klima, U., "Magnetic Vascular Port in Minimally Invasive Direct Coronary Artery Bypass Grafting," Circulation, 2004, II-55-II-60.

Meier, MD, Bernhard, et al., "Contemporary Management of Patent Foramen Ovale," American Heart Association, Inc., Circulation, 2003, vol. 107, pp. 5-9.

Parviainen, M. et al., "A New Biodegradable Stent for the Pancreaticojejunal Anastomosis After Pancreaticoduodenal Resection: in Vitro Examination and Pilot Experiences in Humans", *Pancreas*, vol. 21, No. 1, pp. 14-21, 2000.

Ramanathan, G., et al., "Experimental and Computational Methods for Shape Memory Alloys," 15th ASCE Engineering Mechanics Conference, Jun. 2-5, 2002.

Ruddy, A.C. et al., "Rheological, Mechanical and Thermal Behaviour of Radipaque Filled Polymers", *Polymer Processing Research Centre, School of Chemical Engineering*, Queen's University of Belfast , 5 pages.

Ruiz, et al, "The Puncture Technique: A New Method for Transcatheter Closure of Patent Foramen Ovale," Catheterization and Cardiovascular Interventions, 2001, vol. 53, pp. 369-372.

Shabalovskaya, S., "Surface, Corrosion amd Biocompatibility Aspects of Nitinol as and Implant Material," Bio-Medical Materials and Engineering, 2002, vol. 12, 69-109.

Stockel, "Nitinol Medical Devices and Implants," SMST-2000 Conference Proceedings, 2001, pp. 531-541.

Uchil, J., "Shape Memory Alloys—Characterization Techniques," Pramana—Journal of Physics, 2002, vol. 58(5)(6), pp. 1131-1139.

* cited by examiner

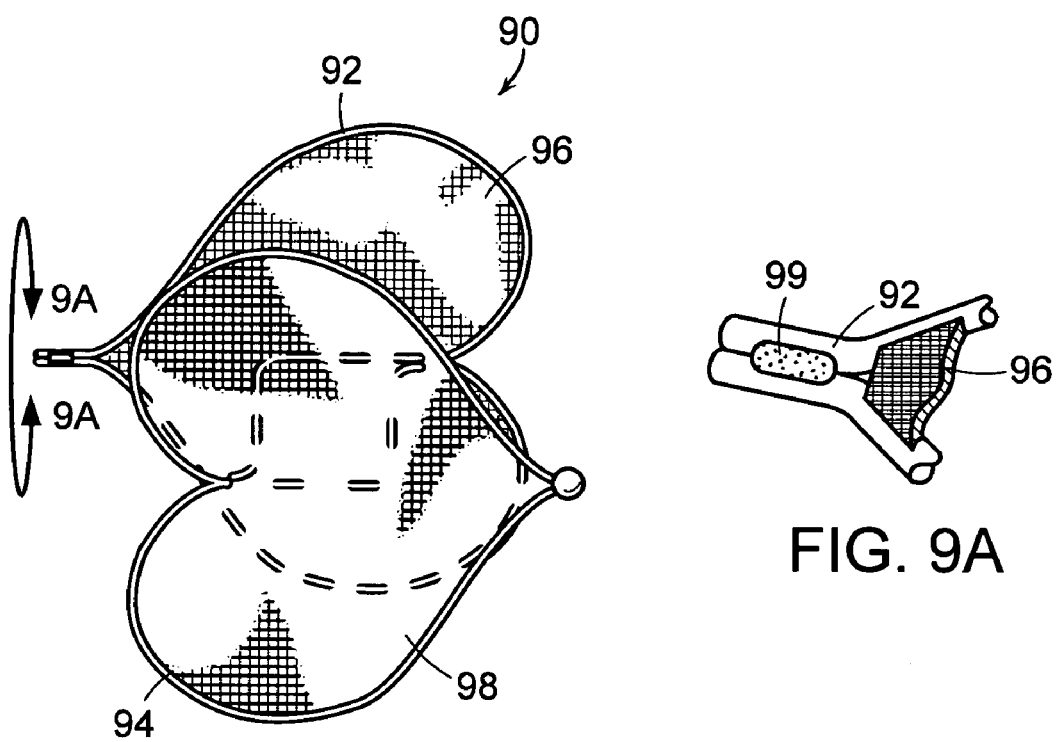
FIG. 9
FIG. 9A
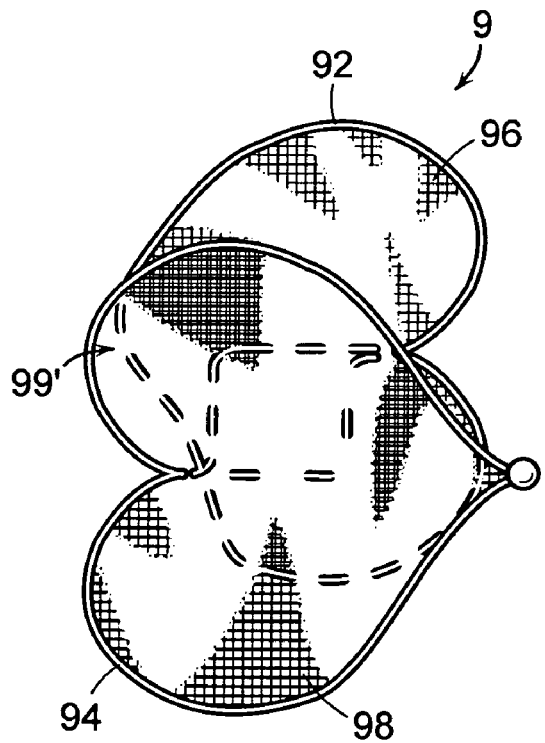
FIG. 9B

HEART-SHAPED PFO CLOSURE DEVICE

CROSS-REFERENCE TO RELATED APPLICATION

This application claims priority to provisional application Ser. No. 60/565,285, filed Apr. 26, 2004, which is incorporated herein by reference.

FIELD OF THE INVENTION

The present invention relates to devices and methods that are used to close defects, and particularly for closing a patent foramen ovale (PFO).

BACKGROUND

A PFO, illustrated in FIG. 1, is a persistent, one-way, usually flap-like opening in the wall between the right atrium 10 and left atrium 12 of the heart. Because left atrial pressure is normally higher than right atrial pressure, the flap formed by septum primum 14 and septum secundum 16 usually stays closed. Under certain conditions, however, right atrial pressure can exceed left atrial pressure, which creates the possibility that blood could pass from the right atrium to the left atrium through a PFO tunnel 18 and allow blood clots to enter the systemic circulation. It would be desirable to avoid this situation.

SUMMARY

Embodiments of the present invention provide a device for closing septal defects, such as a patent foramen ovale (PFO). The device has substantially circular proximal and distal configurations connected with a center joint. In most embodiments, the center joint has a generally square configuration. The shape of the center joint provides for centering of the device in the defect. The device can be made from wire, such as nitinol wire. Pieces of wire can be connected with tubes, welds, or other joining techniques. The device can be retrieved after deployment and repositioned if needed. Either the distal (left atrial) clip, proximal (right atrial) clip, or both can be covered with a tissue scaffold to help the defect seal and to encourage tissue ingrowth.

Embodiments of the closure device can have one or more of the following advantages: an atraumatic shape, good embolization resistance, an ability to conform to the anatomy (instead of the anatomy conforming to the device, especially in the defect tunnel), repositionable or/and removable during delivery, and a small profile after deployment. Other benefits include small diameter delivery sheath, ease of manufacturing, cost effectiveness, and overall simplicity. Other features and advantages will become apparent from the following detailed description and drawings.

BRIEF DESCRIPTION OF THE DRAWINGS

FIGS. 9 and 9A are a perspective view of the device according to another embodiment of the present invention, and an enlarged detailed view of a portion of a that device, respectively. FIG. 9B is a perspective view of an alternative embodiment to that in FIG. 9.

DETAILED DESCRIPTION

Embodiments of the devices described here are intended to clip together tissue flaps, and particularly to clip together septum primum and septum secundum to minimize the flow of blood from the right atrium to the left atrium, thereby helping to reduce the risk of stroke. To accomplish this, the devices apply a compressive force between septum primum and septum secundum to bring septum primum and septum secundum together to provide a closing effect. In at least some embodiments, the applied compressive force draws the more flexible septum primum toward septum secundum, thereby closing the PFO without significantly distorting the septum. The clip can provide mechanical closure at points of contact along the PFO such that the largest remaining opening is reduced to a size deemed small enough to block stroke-inducing embolic particles from crossing through the PFO tunnel. In other embodiments, the clip provides substantially complete closure along the entire PFO length. Because the clips do not distort the defect in preferred embodiments, the overlapping layers of septal tissues may themselves be used to close the defect as they are compressed by the clip.

Figure 2A:
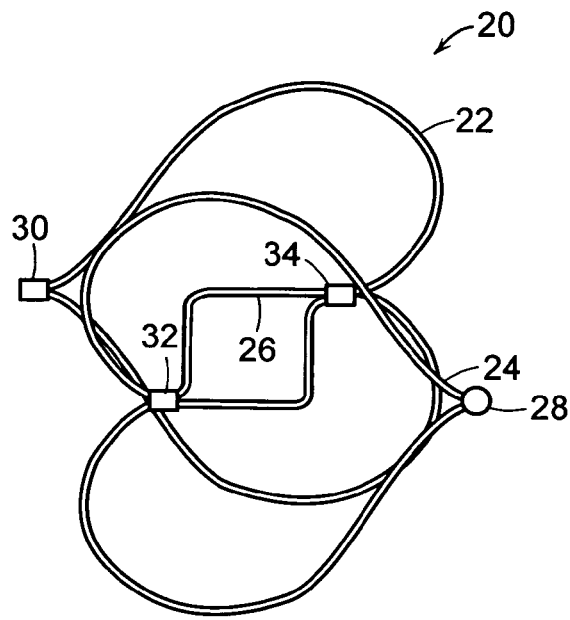
FIGS. 2A and 2B are front elevational and top plan views of a device according to the present invention.
Figure 2B:
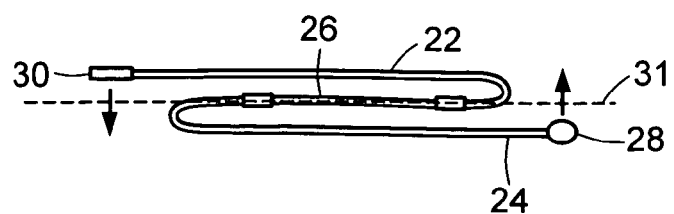
Figure 3A:
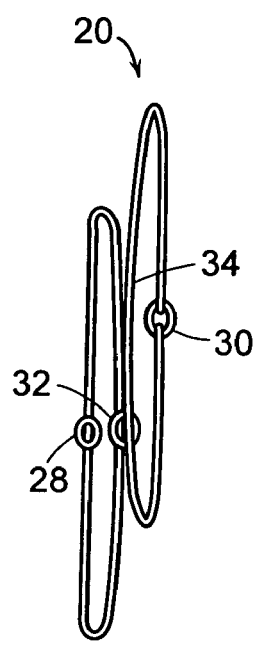
FIGS. 3A and 3B are right side elevational views of the device as made and as positioned in a PFO, respectively.
Figure 3B:
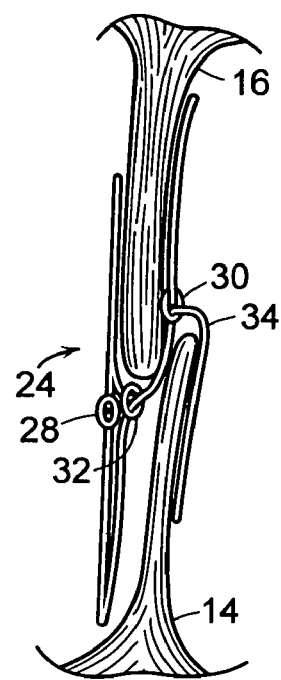
Figure 4:
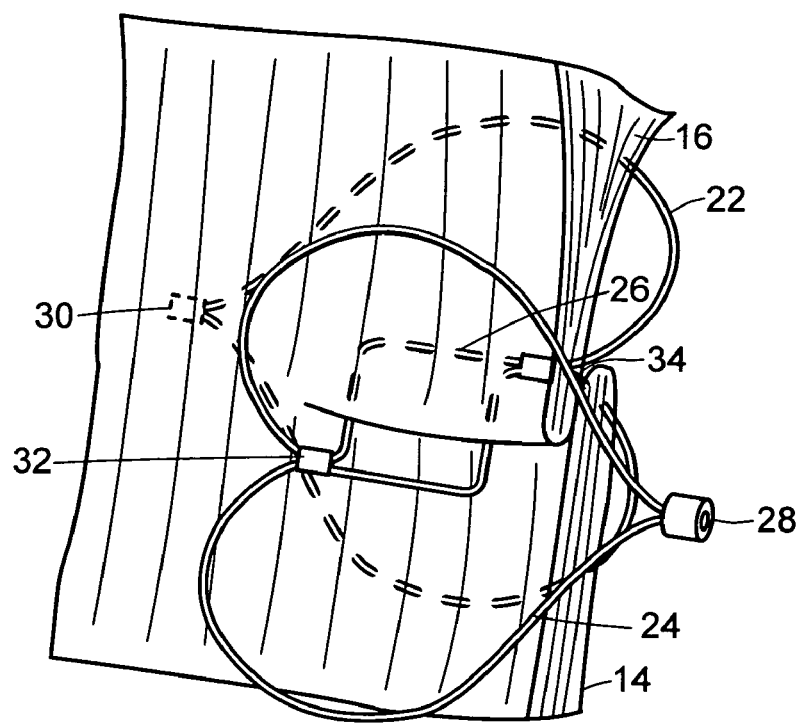
FIG. 4 is a prospective view and FIGS. 5 and 6 are front and rear elevational views showing the device of FIG. 2A as positioned in a PFO.

Referring to FIGS. 2A and 2B, a closure device 20 has a distal loop 22, a proximal loop 24, and a center joint 26 connecting loops 22 and 24. In this embodiment, the loops are each generally "heart-shaped" and have two lobes that come together. As shown in FIG. 2A, there are several points in the device where wires or portions of a wire meet. At these points, the wires can be welded and/or clamped with a collar 28, 30, 32, and 34. Collars 28 and 30 are formed at outer vertices of loops 24 and 22, respectively; collars 32 and 34 are provided where the lobes of the loops come together at center joint 26.

Center joint 26 has generally four sides and is preferably generally rectangular in shape in that it has basically four sides with two sets of parallel sides coming together at roughly right angles. While "rectangular" strictly might imply sharp corners, it should be understood that the corners here can be rounded or have other configurations as are present at the location of collars 32 and 34 as shown in FIG. 2A. The sides can be straight, but can also have some bends or curves while the overall look is still generally rectangular. More preferably, the center joint is generally square. Other shapes could be used, including circular, polygonal, or some combination of straight and curved segments. The two wire paths from collar 32 to collar 34 preferably have about the same length, thus making it easier to load the device in a catheter or sheath.

FIG. 2B shows a top plan view with loops 22 and 24 that are in substantially parallel configuration and parallel to center joint 26 from this view. The device could have this configuration, although it could be formed such that, in its non-deployed configuration, loops 22 and 24 are curved in the vertical plane such that the ends, shown at collars 28 and 30, bend to an opposite side of a center line 31 that runs through center joint 26. In other words, as shown by the arrows in FIG. 2B, loop 24 could start one side of center line 31 and have its outer vertex at collar 28 on the other side of line 31, and similarly for loop 22. This overlapping effect can help provide good compressive force, especially for materials with less recovery. For materials with very high recovery, such as nitinol, such a configuration might not be desirable.

Referring to FIGS. 3A, 3B and 4-6, device 20 is shown in a non-deployed configuration (FIG. 3A), and as deployed (FIGS. 3B and 4-6). As indicated in these views, loops 22 and 24 each have a respective upper portion or top lobe in contact with septum secundum 16 and a lower portion or lower lobe in contact with septum primum 14. The loops generally define a plane that is generally parallel to each of septum primum and septum secundum. This configuration helps distribute compressive forces across the applicable septum and makes the pressure less traumatic.

Figure 1:
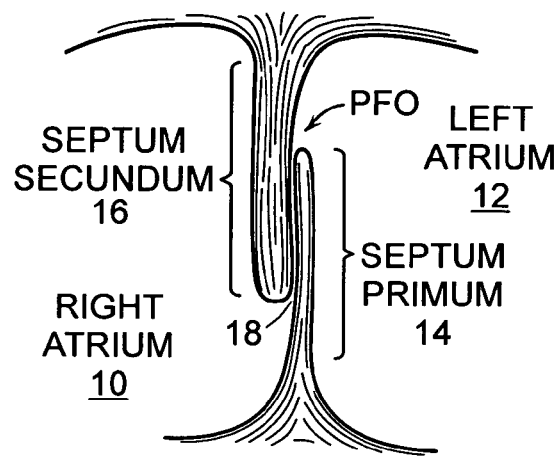
FIG. 1 is a cross-sectional side view showing a patent foreman ovale (PFO).
Figure 5:
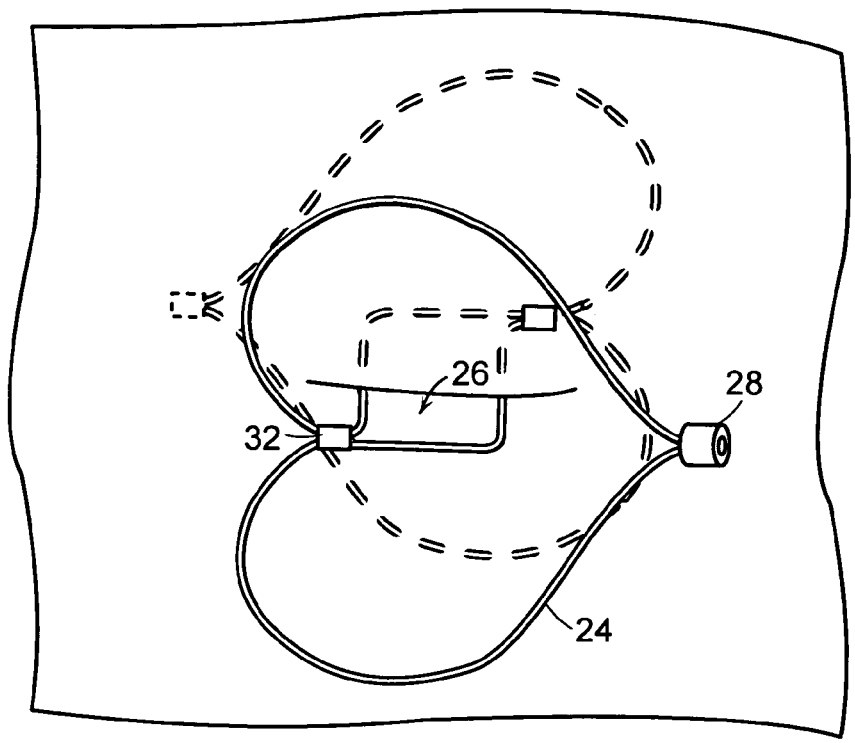
Figure 6:
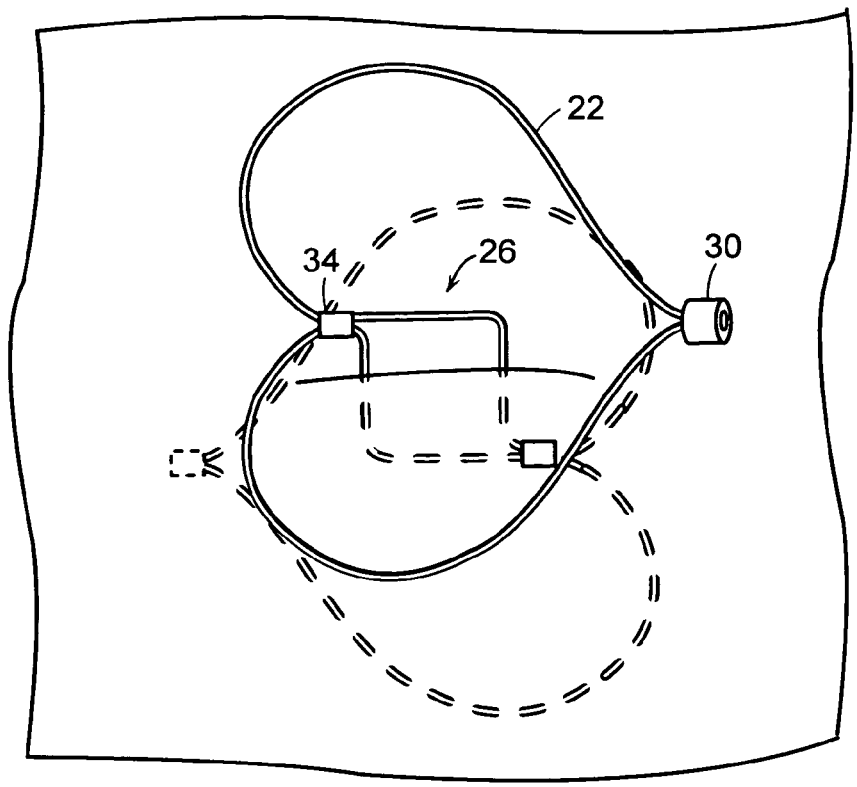

As shown particularly in FIGS. 5 and 6, which represent views from the right atrium (FIG. 5) and left atrium (FIG. 6), center joint 26 is partially on the right atrial side, partially on the left atrial side, and partially within PFO tunnel 18 (FIG. 1) where the flaps of septum secundum 16 (FIG. 4) and septum primum 14 (FIG. 4) overlap. The center joint could be completely within the overlapping portions of septum primum and septum secundum.

The loops and center joint are formed with appropriate dimensions and materials, and in such a configuration, such that when deployed, the loops provide a compressive force that holds together septum primum 14 and septum secundum 16.

Figure 7:
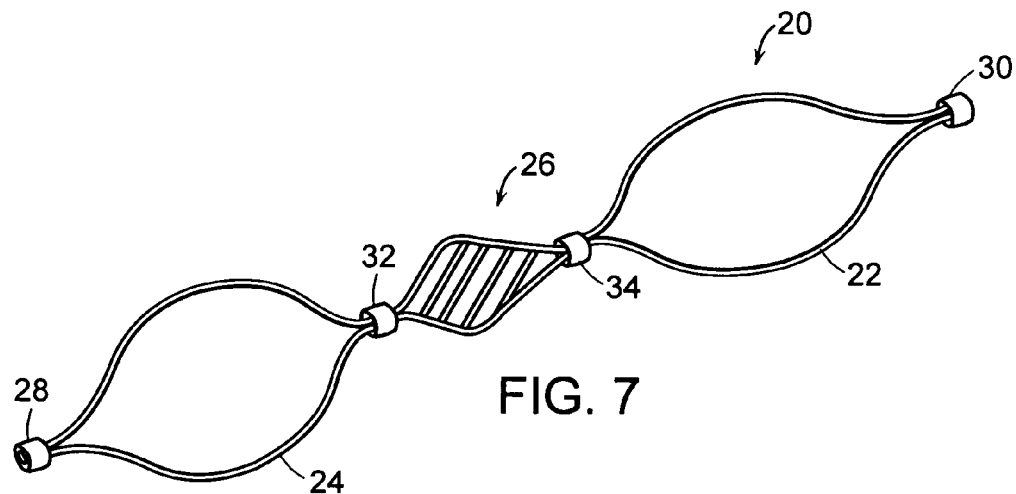
FIGS. 7 and 8 are views of the device in an elongated form and shown within a catheter for delivery.
Figure 8:
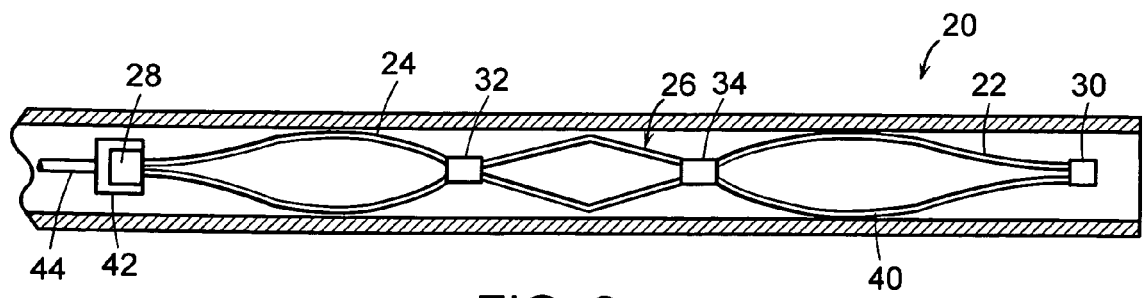

Referring to FIGS. 7 and 8, the device can be deployed with a delivery sheath in the generally conventional manner. FIGS. 7 and 8 show device 20 in an elongated form for delivery purposes. Device 20 can be provided with a low profile to fit within a sheath 40 and have an end, such as at collar 28, in a contact with a connector 42 at the end of a wire 44 that is used by an operator to push the device or hold the device as sheath 40 is retracted, i.e., the connection allows relative movement between device 20 and sheath 40. Typically, device 20 is deployed by providing sheath 40 within the left atrium and withdrawing sheath 40 while wire 44 and connector 42 hold device 20 in place. As sheath 40 is withdrawn, loop 22 opens and assumes the shape shown in FIG. 6. Sheath 40 is further drawn back within the PFO tunnel to release center joint 26, and then is further drawn back into the right atrium to allow loop 24 to open in the right atrium. Connector 42 can stay in contact until the device is at a desired positioning of device 20. If the operator is not satisfied with the positioning of device 20, the connector can be used to pull the device or hold the device while the sheath is pushed forward to draw the device back into the sheath to be removed or redeployed.

Figure 7A:
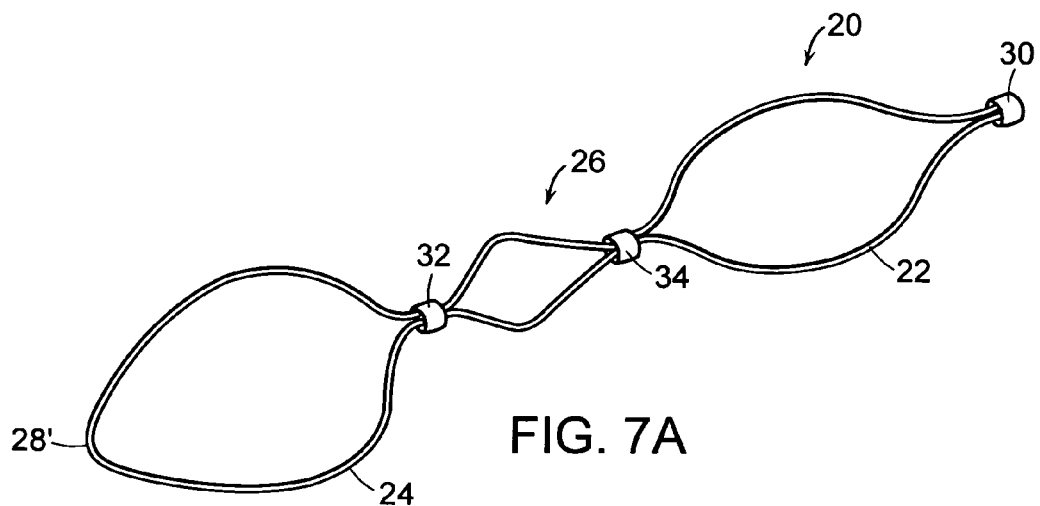
FIG. 7A is a perspective view of an alternative embodiment to FIG. 7.

FIG. 7A shows an embodiment that is similar to that of FIG. 7, except that rather than a collar 28, there is a curved portion 28' in the wire used to form loop 24. While shown as a more gradual bend, it could have a sharper bend, such as a hairpin turn. A curved portion without a collar could be used on the other side where collar 30 is, and in other embodiments where a collar is shown.

FIGS. 9 and 9A show another embodiment of the present invention. In this embodiment, device 90 has a loop 92 for use in the left atrium and loop 94 for use in the right atrium. A tissue scaffold 96 is shown within loop 92 for deployment in the left atrium, and a scaffold is shown connected to loop 94 to be released in the right atrium. As shown in FIG. 9A, where two portions of wire come together in loop 92, a weld 99 is formed to hold the wires together. As also indicated here, tissue scaffold 96 is shown attached to the wire over most of its distance up to where the wires come together. This device would be delivered in a manner similar to that shown in FIGS. 7 and 8 above. FIG. 9B shows a variation of FIG. 9 in which the weld 99 between two wires is replaced with a curved wire 99' without the weld.

Figure 10:
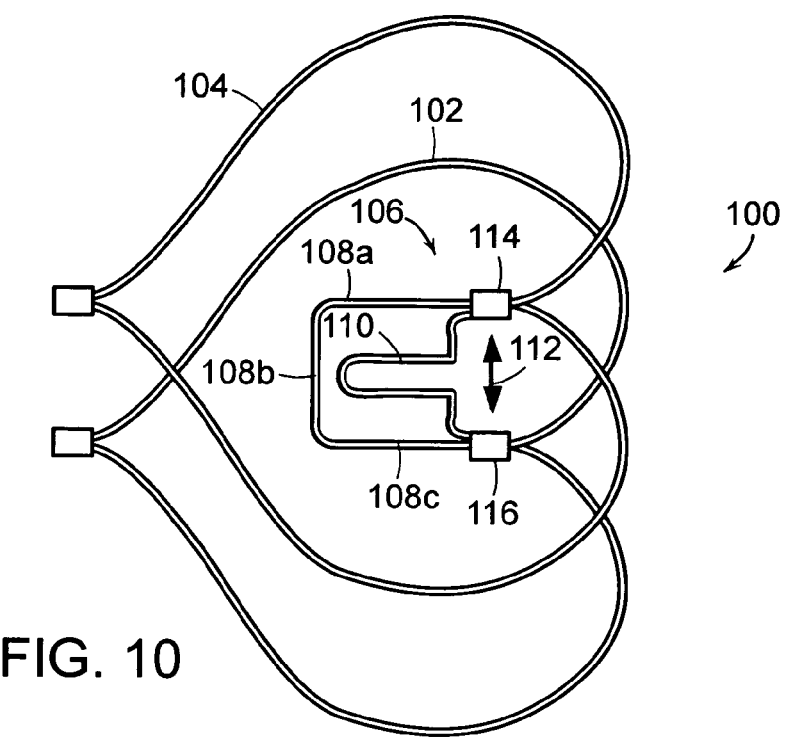
FIG. 10 is a front elevational view of a device according to get another embodiment of the present invention.

Referring to FIG. 10, in another embodiment of the present invention, a device 100 has two heart shaped loops 102 and 104, with a center joint 106 between them. In this case, the center joint has contact points 114, 116 for each of the loops at adjacent corners rather than being at diagonally opposite corners as shown in device 20 in FIG. 2A. This configuration can improve rotational stability compared to the diagonal configuration (i.e., the device is less likely to rotate within the PFO tunnel).

Center joint 106 has three similar sides 108a, 108b, and 108c forming a generally block-U shape. Rather than another similar side, however, a connector 110 is provided that allows for some flexing motion in the direction indicated by arrow 112, and that approximately equalizes the length of the two paths between contact points 114 and 116. These equal paths make it easier to load the device into a sheath or catheter.

Figure 10A:
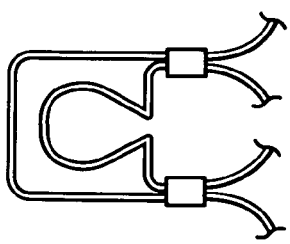
FIGS. 10A-10C are elevational views of alternative configurations for a center joint in the device of FIG. 10.
Figure 10B:
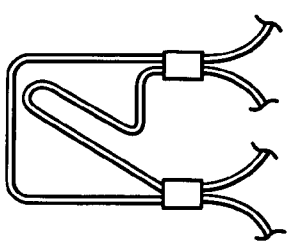
Figure 10C:
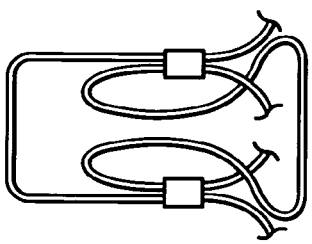

Alternative connections to connection 110 are shown in FIGS. 10A, 10B, and 10C. These figures show various alternative configurations of wires that form loops and angles that allow some ability for sides 108a, 108b, 108c, and 110 to pivot with respect to one or more of the other sides, and that equalize the two path lengths of wires between contact points 114 and 116, thereby helping to make it easier to load the device into a sheath or catheter when it is elongated to a smaller profile.

Figure 11A:
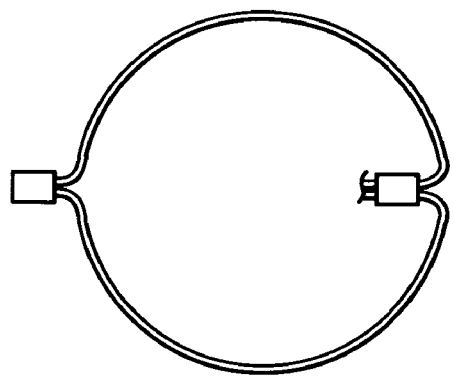
FIGS. 11A-11F are fragmentary front elevational views showing alternative loop designs.
Figure 11B:
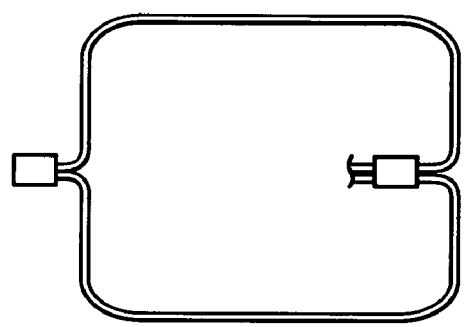
Figure 11C:
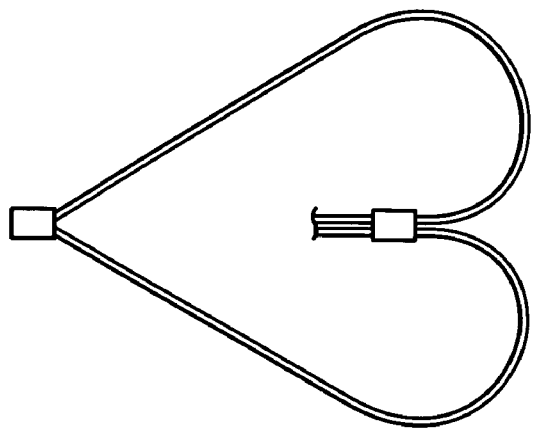
Figure 11D:
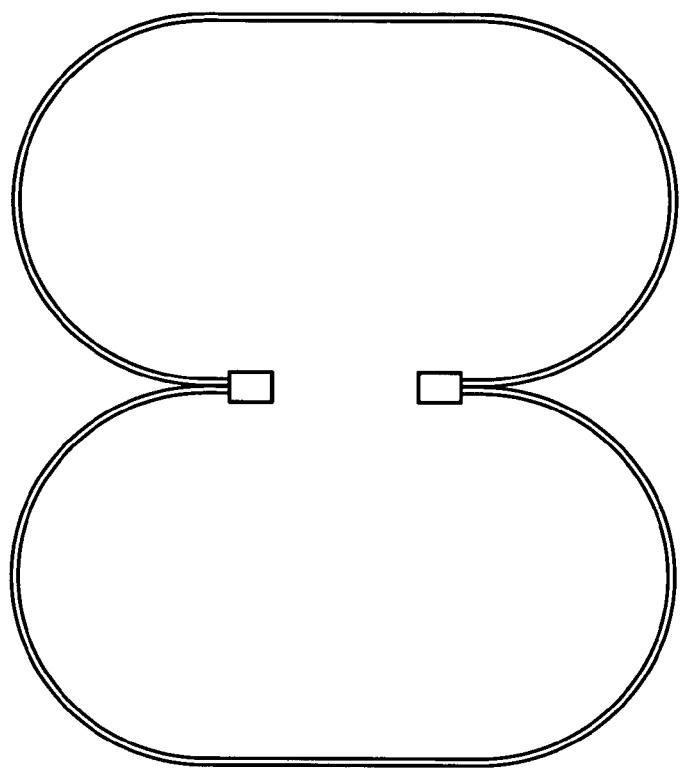
Figure 11E:
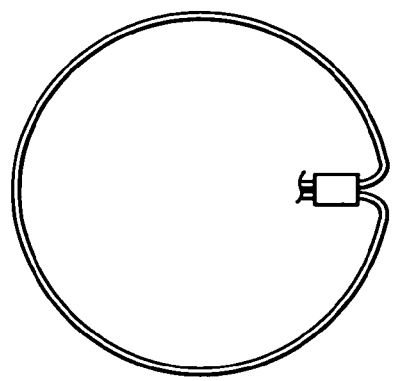
Figure 11F:
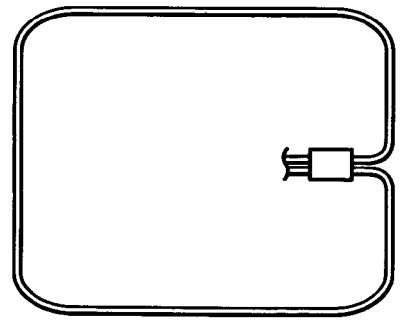

FIGS. 11A-11E show alternative loop configurations. These include a generally circular configuration with two collars (FIG. 11A), a generally rectangular configuration with two collars (FIG. 11B), a heart-shape with straight lines converging on a vertex to provide a more triangular shape (FIG. 11C) than other configuration, such as that shown in FIG. 2A, a FIG. 8 (FIG. 11D), a generally circular configuration with one collars (FIG. 11E), and a generally rectangular configuration with one collar (FIG. 11F). Other shapes could be used, although it is preferred (but not required) that the wires do not cross in a way that would create rubbing contact.

In most of these embodiments, a single wire could be used with several double-backs, or multiple wires could be used and welded or crimped together with a collar at desired locations. The clips can be formed of metal or nonmetallic materials, including bioresorbable polymers, spring steel, shape memory materials (e.g. nitinol), bioresorbable shape memory polymers, or combinations of the foregoing materials.

Shape memory materials are useful for this application. These materials allow the clips to resume and maintain their intended shape following deployment in vivo. A clip may take advantage of the thermal shape memory properties of a shape memory material, the superelastic properties of a shape memory material, or some combination of the two. In other particular embodiments, the clips are cut into their desired shapes from sheets of material, such as from bioresorbable shape memory polymers.

The first and second loops are preferably made from a material or are configured to apply a compressive force to the overlapping layers of septal tissue. The movement of the at least two loops may be limited by the edges of the PFO tunnel (which is usually between 1 mm and 20 mm wide), thereby ensuring the clip device remains horizontally centered across the defect and consistently applies compressive force to the septal tissues at the locations necessary to effect closure of the defect. Accurate and consistent application of localized force can allow the use of a smaller closure device.

The closure loops of a clip may take various forms depending, in part, on the distribution of force desired to effect closure of a given defect. In this application, the term "defect" is applied to any anatomical configuration requiring treatment. In particular, the defect can be a PFO which may allow, or allows, blood to flow from the right atrium to the left atrium. The shape of each closure member determines the location(s) at which the compressive force is applied to the overlapping layers of septal tissue.

Any of the embodiments of the present invention can include a tissue scaffold on one or both closure members and/or the center joint. The tissue scaffold promotes encapsulation and endothelialization, thereby further encouraging anatomical closure of septum primum and septum secundum. A tissue scaffold can be formed of any flexible, biocompatible material capable of promoting tissue ingrowth, including but not limited to polyester fabrics, Teflon-based materials, such as ePTFE, polyurethanes, metallic materials, polyvinyl alcohol (PVA), extracellular matrix (ECM) or other bioengineered material, synthetic bioabsorbable polymeric scaffolds, other natural materials (e.g. collagen), or combinations of these materials. Also, a tissue scaffold may be formed of a thin metallic film or foil. The scaffold may be attached to one or both sides of the device. A tissue scaffold or the frame may contain drugs or biological agents to improve the defect healing process and/or to prevent clotting.

The center joint serves a horizontal centering function. Specifically, the connecting members may be designed to fit within the PFO tunnel such that there is little (or no) horizontal movement once the device is deployed. Horizontal centering is desirable because the dynamic conditions in the heart may tend to move the device. Other configurations, including bent or slightly bent wires, to position the connecting members within the PFO tunnel can be used.

The compressive force applied by the closure members of any of the various embodiments described herein can be adjusted in a variety of ways. For example, the thickness of a strand or wire can be increased or decreased to adjust the compressive force. In general (and with other design considerations similar), a thicker strand or wire will provide higher compressive force. Additionally, various closure member configurations may be chosen to increase the compressive force. Generally, bends with smaller angles will provide more compressive force. Different parts of the device can be treated in a different manner to alter stiffness and recovery, as described in applicable Ser. No. 10/702,717 filed Nov. 6, 2003, which is incorporated herein by reference.

In some general respects, such as the ability to use one wire, the devices described here have some general similarities to some devices in application Ser. No. 10/396,253, filed Mar. 25, 2003, published as 2003/0225421, which is incorporated herein be reference.

Having described embodiments of the present invention, it should be apparent that the invention is capable of other and different embodiments and may be modified in various respects, all without departing from the scope of the invention as defined by the appended claims. Accordingly, the foregoing drawings and description are to be regarded as illustrative in nature and not in a restrictive or limiting sense.

What is claimed is:

1. An occluder device for closing two overlapping layers of septum primum and septum secundum dividing a left atrium and a right atrium in a mammalian heart, comprising:
   first and second opposed closure members configured to be disposed on opposite sides of the septum, each of said closure members generally defining a plane with a periphery, wherein the planes are configured to be generally parallel to each of septum primum and septum secundum; and
   a center joint connecting the first and second opposed closure members, the center joint comprising pairs of parallel wire paths and at least two collars having first and second opposing ends, wherein each wire path begins at the first end of a first collar and terminates at a first end of a second collar, wherein further each wire path forms a center vertex between the collars;
   wherein the center joint is configured so the center vertex of each wire path extends between the overlapping layers of septum primum and septum secundum leaving the collars and closure members outside the layers, wherein further at least one of said closure members has a generally heart shape and includes two lobes that come together at the center joint, the lobes having contact points at adjacent corners to provide a compressive force to the overlapping layers of septum primum and septum secundum wherein said closure members are configured to prevent the device from moving along a longitudinal axis formed by the passage between septum primum and septum secundum when the device is deployed.

2. The device of claim 1, wherein said first closure member is sized and shaped to apply a compressive force to the layers of septum primum and septum secundum in the right atrium, and said second closure member is sized and shaped to apply a compressive force to the layers of septum primum and septum secundum in the left atrium.

3. The device of claim 1, wherein the device includes a material selected from the group consisting of metals, non-metallic materials, bioresorbable polymers, spring steel, shape memory materials, bioresorbable shape memory polymers, and combinations thereof.

4. The device of claim 3, wherein the device is constituted at least in part of nitinol.

5. The device of claim 1, wherein each of said closure members has a generally heart shape including two lobes that come together at the center joint.

6. The device of claim 1, wherein at least one of said closure members is a loop.

7. A delivery assembly comprising a catheter and the device according to claim 1, wherein the catheter contains the device in an elongated form.

* * * * *